(12) United States Patent
Hessler et al.

(10) Patent No.: US 8,281,974 B2
(45) Date of Patent: Oct. 9, 2012

(54) SURGICAL STAPLER WITH SUTURE LOCATOR

(75) Inventors: Thomas R. Hessler, Bethel, CT (US); Thomas Wenchell, Durham, CT (US)

(73) Assignee: Tyco Healthcare, Group LP, Mansfield, MA (US)

( * ) Notice: Subject to any disclaimer, the term of this patent is extended or adjusted under 35 U.S.C. 154(b) by 326 days.

(21) Appl. No.: 12/683,477

(22) Filed: Jan. 7, 2010

(65) Prior Publication Data

US 2010/0176181 A1 Jul. 15, 2010

Related U.S. Application Data

(60) Provisional application No. 61/144,488, filed on Jan. 14, 2009.

(51) Int. Cl.
*A61B 17/068* (2006.01)

(52) U.S. Cl. ............. 227/179.1; 227/175.1; 227/19

(58) Field of Classification Search ............. 227/179.1, 227/175.1, 19
See application file for complete search history.

(56) References Cited

U.S. PATENT DOCUMENTS

| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |

(Continued)

FOREIGN PATENT DOCUMENTS

CA 908529 8/1972

(Continued)

*Primary Examiner* — Brian D Nash

(57) ABSTRACT

An anvil assembly comprising an anvil shaft and an anvil head, the anvil head having anvil depressions for forming surgical staples, and the anvil head mounted to the anvil shaft. The anvil shaft has a longitudinal axis and a helical slot formed therein. A disc is movable along the slot to a selected position to selectively adjust the positioning of a purse string suture.

11 Claims, 7 Drawing Sheets

U.S. PATENT DOCUMENTS

| | | | |
|---|---|---|---|
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,622 A | 1/1990 | Green et al. | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,271,543 A | 12/1993 | Grant et al. | |
| 5,271,544 A | 12/1993 | Fox et al. | |
| 5,275,322 A | 1/1994 | Brinkerhoff et al. | |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main et al. | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A * | 3/1995 | Kuramoto et al. | 227/179.1 |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A * | 9/2000 | Ravo et al. | 606/153 |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balázs et al. | |
| 6,264,086 B1 | 7/2001 | McGuckin, Jr. | |
| 6,269,997 B1 | 8/2001 | Balázs et al. | |
| 6,273,897 B1 | 8/2001 | Dalessandro et al. | |
| 6,279,809 B1 | 8/2001 | Nicolo | |
| 6,302,311 B1 | 10/2001 | Adams et al. | |
| 6,338,737 B1 | 1/2002 | Toledano | |
| 6,343,731 B1 | 2/2002 | Adams et al. | |
| 6,387,105 B1 | 5/2002 | Gifford, III et al. | |
| 6,398,795 B1 | 6/2002 | McAlister et al. | |
| 6,402,008 B1 | 6/2002 | Lucas | |
| 6,439,446 B1 | 8/2002 | Perry et al. | |
| 6,443,973 B1 | 9/2002 | Whitman | |
| 6,450,390 B2 | 9/2002 | Heck et al. | |
| 6,478,210 B2 | 11/2002 | Adams et al. | |
| 6,488,197 B1 | 12/2002 | Whitman | |
| 6,491,201 B1 | 12/2002 | Whitman | |
| 6,494,877 B2 | 12/2002 | Odell et al. | |
| 6,503,259 B2 | 1/2003 | Huxel et al. | |
| 6,517,566 B1 | 2/2003 | Hovland et al. | |
| 6,520,398 B2 | 2/2003 | Nicolo | |
| 6,533,157 B1 | 3/2003 | Whitman | |
| 6,551,334 B2 | 4/2003 | Blatter et al. | |
| 6,578,751 B2 | 6/2003 | Hartwick | |
| 6,585,144 B2 | 7/2003 | Adams et al. | |
| 6,588,643 B2 | 7/2003 | Bolduc et al. | |
| 6,592,596 B1 | 7/2003 | Geitz | |
| 6,601,749 B2 | 8/2003 | Sullivan et al. | |
| 6,605,078 B2 | 8/2003 | Adams | |
| 6,605,098 B2 | 8/2003 | Nobis et al. | |
| 6,626,921 B2 | 9/2003 | Blatter et al. | |
| 6,629,630 B2 | 10/2003 | Adams | |
| 6,631,837 B1 | 10/2003 | Heck | |
| 6,632,227 B2 | 10/2003 | Adams | |
| 6,632,237 B2 | 10/2003 | Ben-David et al. | |
| 6,652,542 B2 | 11/2003 | Blatter et al. | |
| 6,659,327 B2 | 12/2003 | Heck et al. | |
| 6,676,671 B2 | 1/2004 | Robertson et al. | |
| 6,681,979 B2 | 1/2004 | Whitman | |
| 6,685,079 B2 | 2/2004 | Sharma et al. | |
| 6,695,198 B2 | 2/2004 | Adams et al. | |

| | | |
|---|---|---|
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, Iii et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 2003/0111507 A1 | 6/2003 | Nunez |
| 2005/0021053 A1* | 1/2005 | Heinrich ............ 606/139 |
| 2005/0051597 A1 | 3/2005 | Toledano |
| 2005/0059996 A1 | 3/2005 | Bauman et al. |
| 2005/0059997 A1 | 3/2005 | Bauman et al. |
| 2005/0107813 A1 | 5/2005 | Gilete Garcia |
| 2005/0125009 A1 | 6/2005 | Perry et al. |
| 2005/0145674 A1 | 7/2005 | Sonnenschein et al. |
| 2005/0145675 A1 | 7/2005 | Hartwick et al. |
| 2005/0205640 A1* | 9/2005 | Milliman ............ 227/176.1 |
| 2006/0000869 A1 | 1/2006 | Fontayne |
| 2006/0011698 A1 | 1/2006 | Okada et al. |
| 2006/0047307 A1 | 3/2006 | Ortiz et al. |
| 2006/0108393 A1 | 5/2006 | Heinrich et al. |

| | | |
|---|---|---|
| 2006/0144897 A1 | 7/2006 | Jankowski et al. |
| 2006/0201989 A1 | 9/2006 | Ojeda |
| 2006/0241692 A1 | 10/2006 | McGuckin, Jr. et al. |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0230170 A1 | 9/2009 | Milliman |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0255976 A1 | 10/2009 | Marczyk et al. |
| 2009/0302089 A1 | 12/2009 | Harari et al. |
| 2010/0001037 A1 | 1/2010 | Racenet et al. |
| 2010/0019016 A1 | 1/2010 | Edoga et al. |
| 2010/0038401 A1 | 2/2010 | Milliman et al. |
| 2010/0051668 A1* | 3/2010 | Milliman et al. .......... 227/175.1 |
| 2010/0065607 A1 | 3/2010 | Orban, III et al. |
| 2010/0084453 A1 | 4/2010 | Hu |
| 2010/0089971 A1* | 4/2010 | Milliman et al. .......... 227/175.1 |
| 2010/0108739 A1 | 5/2010 | Holsten et al. |
| 2010/0108740 A1 | 5/2010 | Pastorelli et al. |
| 2010/0108741 A1* | 5/2010 | Hessler et al. ............. 227/179.1 |
| 2010/0133319 A1* | 6/2010 | Milliman et al. .......... 227/175.1 |
| 2010/0147923 A1 | 6/2010 | D'Agostino et al. |
| 2010/0163598 A1 | 7/2010 | Belzer |
| 2010/0170932 A1 | 7/2010 | Wenchell et al. |
| 2010/0176181 A1* | 7/2010 | Hessler et al. ............. 227/175.1 |
| 2010/0224668 A1 | 9/2010 | Fontayne et al. |
| 2010/0230465 A1 | 9/2010 | Smith et al. |
| 2010/0230466 A1 | 9/2010 | Criscuolo et al. |
| 2010/0230467 A1 | 9/2010 | Criscuolo et al. |
| 2010/0258611 A1 | 10/2010 | Smith et al. |
| 2010/0264195 A1 | 10/2010 | Bettuchi |
| 2010/0270356 A1 | 10/2010 | Holsten et al. |
| 2010/0282815 A1 | 11/2010 | Bettuchi et al. |
| 2010/0301098 A1 | 12/2010 | Kostrzewski |
| 2010/0327041 A1 | 12/2010 | Milliman et al. |
| 2011/0006100 A1 | 1/2011 | Milliam |
| 2011/0006102 A1 | 1/2011 | Kostrzewski |
| 2011/0006104 A1 | 1/2011 | Felix |
| 2011/0011916 A1 | 1/2011 | Levine |
| 2011/0017800 A1 | 1/2011 | Viola |
| 2011/0024476 A1 | 2/2011 | Bettuchi et al. |
| 2011/0024481 A1 | 2/2011 | Bettuchi et al. |
| 2011/0036889 A1 | 2/2011 | Heinrich et al. |
| 2011/0036894 A1 | 2/2011 | Bettuchi |
| 2011/0042442 A1 | 2/2011 | Viola et al. |
| 2011/0042443 A1 | 2/2011 | Milliman et al. |
| 2011/0057016 A1 | 3/2011 | Bettuchi |
| 2011/0089219 A1 | 4/2011 | Hessler |
| 2011/0095067 A1 | 4/2011 | Ohdaira |
| 2011/0095068 A1 | 4/2011 | Patel |
| 2011/0095069 A1 | 4/2011 | Patel et al. |
| 2011/0095070 A1 | 4/2011 | Patel et al. |
| 2011/0101065 A1 | 5/2011 | Milliman |
| 2011/0114697 A1 | 5/2011 | Baxter, III et al. |
| 2011/0114698 A1 | 5/2011 | Baxter, III et al. |
| 2011/0114699 A1 | 5/2011 | Baxter, III et al. |
| 2011/0114700 A1 | 5/2011 | Baxter, III et al. |
| 2011/0114701 A1 | 5/2011 | Hessler |
| 2011/0118761 A1 | 5/2011 | Baxter, III et al. |
| 2011/0130788 A1 | 6/2011 | Orban, III et al. |
| 2011/0139852 A1 | 6/2011 | Zingman |
| 2011/0139853 A1 | 6/2011 | Viola |
| 2011/0144640 A1 | 6/2011 | Heinrich et al. |
| 2011/0147432 A1 | 6/2011 | Heinrich et al. |
| 2011/0147434 A1 | 6/2011 | Hueil et al. |
| 2011/0147435 A1 | 6/2011 | Heinrich et al. |
| 2011/0192882 A1 | 8/2011 | Hess et al. |
| 2011/0210156 A1 | 9/2011 | Smith et al. |
| 2011/0220703 A1 | 9/2011 | Orban, III |
| 2011/0248067 A1 | 10/2011 | Takei |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 0594436 | 10/1993 |
| EP | 1354560 A2 | 10/2003 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 | 1/1988 |
| WO | 8706448 | 11/1987 |
| WO | WO 8706448 A | 11/1987 |
| WO | WO 8900406 A1 | 1/1989 |
| WO | WO 9006085 A1 | 6/1990 |
| WO | 2008107918 | 9/2008 |

* cited by examiner

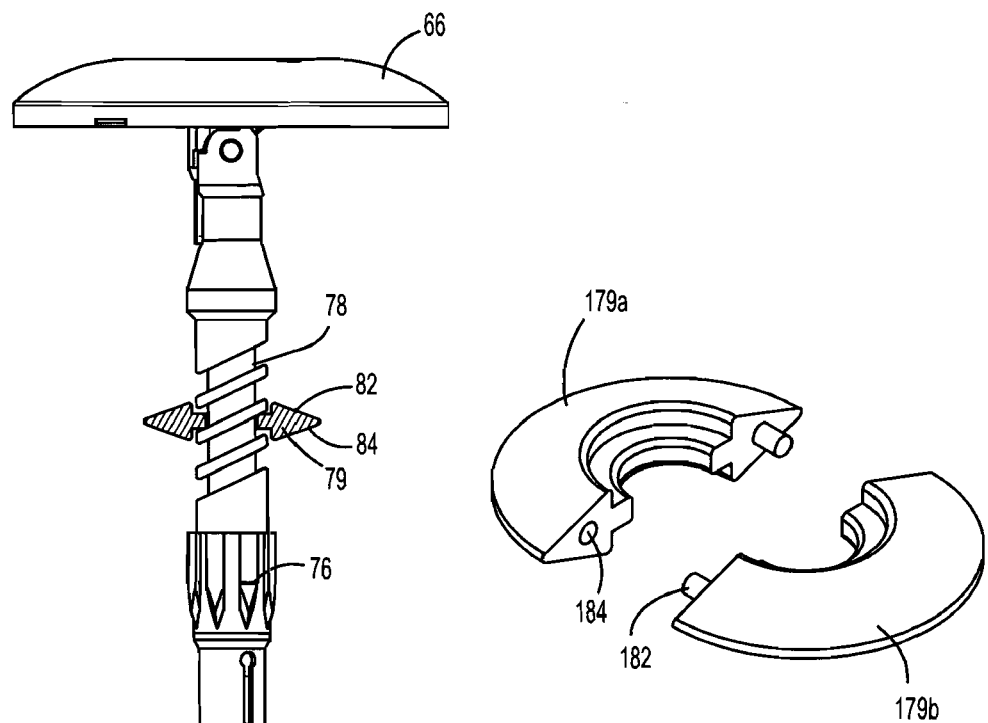
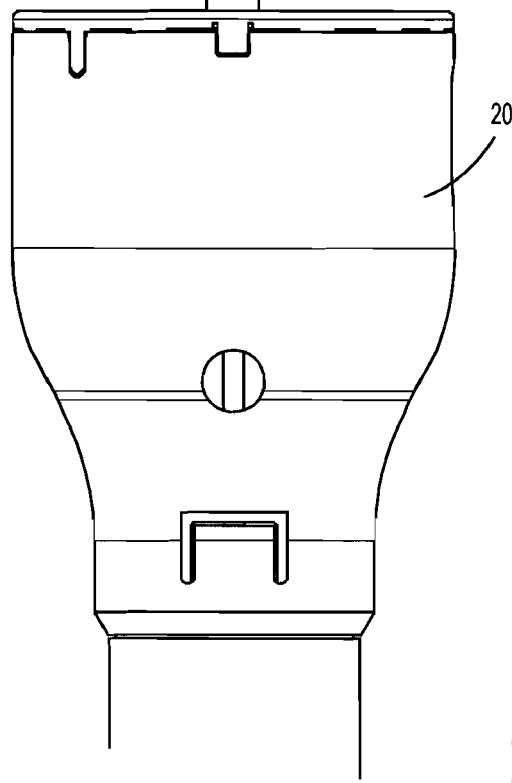
FIG. 4
FIG. 5

SURGICAL STAPLER WITH SUTURE LOCATOR

This application claims priority from provisional application Ser. No. 61/144,488, filed Jan. 14, 2009, the entire contents of which are incorporated herein by reference.

BACKGROUND

1. Technical Field

The present disclosure relates to a surgical stapling device and more particularly to a surgical stapling device suitable for treatment of internal hemorrhoids.

2. Background of Related Art

Anastomosis is the surgical joining of separate hollow organ sections. In known circular anastomosis procedures, two ends of organ sections are joined by means of a stapling device which drives a circular array of staples through each organ section and simultaneously cores any tissue interior of the driven circular array of staples to free a tubular passage. Examples of such devices are described in U.S. Pat. Nos. 7,234,624, 6,945,444, 6,053,390, 5,588,579, 5,119,983, 4,646,745, 4,576,167, 4,473,077.

Typically the circular stapling device has an elongated shaft having a handle portion at a proximal end and a staple cartridge at a distal end. An anvil assembly including an anvil rod with an attached anvil head is mounted to the distal end of the device. The anvil is approximated to clamp tissue between the staple holding component and the anvil. The clamped tissue is stapled by actuation of the handle portion to drive circular arrays of staples through the tissue and into anvil depressions on the anvil head to form the staples. An annular knife is advanced with the handle actuation to core tissue inboard of the staple array.

Surgical stapling devices for performing circular anastomosis have also been used to treat hemorrhoids in the rectum. Hemorrhoids are masses of tissue in the anus containing enlarged blood vessels. Internal hemorrhoids are inside the anal canal; external hemorrhoids lie outside the anal canal. Hemorrhoidectomy is a surgical procedure in which the hemorrhoids are removed. Stapled hemorrhoidopexy is a surgical procedure in which a stapling device is used to remove tissue just above the hemorrhoids in order to pull the hemorrhoids back up inside the rectum and reduce the symptoms. The staples interrupt the blood flow of the superior hemorrhoidal arterial branches, cutting off the blood supply, thus causing the hemorrhoids to shrink. This is used for treatment of internal hemorrhoids.

During the use of a circular stapling device for hemorrhoid treatment, the anvil head and the staple holding component of the device are inserted through and into the rectum with the anvil head and the stapling holding component in an open or unapproximated position. Thereafter, a purse string suture is used to pull the internal hemorrhoidal tissue and/or mucosal tissue toward the anvil rod. Next, the anvil head and the staple holding component are approximated to clamp the hemorrhoidal tissue and/or mucosal tissue between the anvil head and the staple holding component. The stapling device is fired to remove the hemorrhoidal tissue and/or mucosal tissue and staple the cut tissue.

It would be advantageous to provide a device with an option to adjust the amount of tissue for purse stringing to enhance control over the amount of tissue removed.

SUMMARY

The present disclosure provides an anvil assembly comprising an anvil shaft and an anvil head, the anvil head having anvil depressions for forming surgical staples. The anvil head is mounted to the anvil shaft. The anvil shaft has a longitudinal axis and a helical slot formed therein. A rotatable disc composed of two separate components is movable along the slot to a selected position to selectively adjust the amount of tissue for purse stringing. The disc can also be used to adjust the tension on a purse string suture placed about the anvil shaft. The disc has an internal thread to threadingly engage the helical slot of the anvil shaft.

In one embodiment, the two components of the disc are attached by a pin and slot arrangement.

The anvil assembly preferably has a mounting structure on the anvil shaft for releasably mounting the anvil shaft to a stapling instrument.

The present disclosure also provides a surgical stapler comprising a handle assembly, an elongated body portion extending distally from the handle assembly and a head portion disposed adjacent a distal end of the elongated body portion and including an anvil assembly and a shell assembly. The anvil assembly is movable in relation to the shell assembly between spaced and approximated positions. The anvil assembly has an anvil head and an anvil shaft with a helical slot formed therein. A rotatable disc composed of two components attachable to each other is movable along the helical slot to a selected position to adjust the amount of tissue drawn into the shell assembly by a purse string suture.

In a preferred embodiment, the anvil shaft is removably mounted to an anvil retainer of the stapler.

BRIEF DESCRIPTION OF THE DRAWINGS

Various embodiments of the present disclosure are described hereinbelow with references to the drawings, wherein:

FIG. 4 is a perspective view of an alternate embodiment of the disc composed of two attachable components;

FIG. 5 is a close up side view of the anvil assembly and shell assembly of FIG. 1 with the disc shown in cross-section.

DETAILED DESCRIPTION OF EMBODIMENTS

Figure 1:
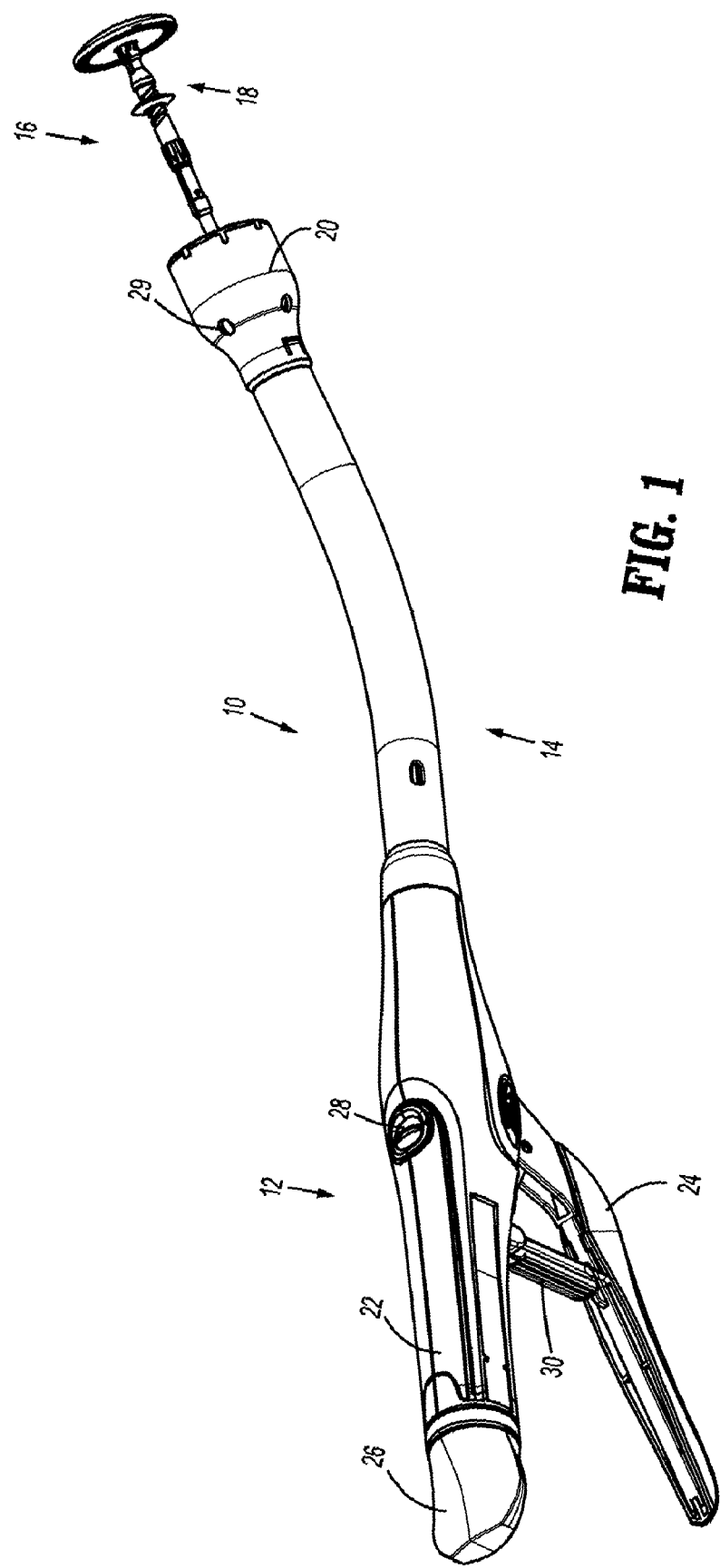
FIG. 1 is a perspective view of a first embodiment of the surgical stapler of the present disclosure.

The presently disclosed surgical stapler will now be described in detail with reference to the drawings in which like reference numerals designate identical or corresponding elements in each of the several views. Throughout this description, the term "proximal" will refer to the portion of the stapler closer to the operator and the term "distal" will refer to the portion of the instrument further from the operator. The presently disclosed stapler is particularly suited for surgical procedures for the treatment of colon prolapse and hemorrhoids, although it can be used for other procedures.

Figure 1A:
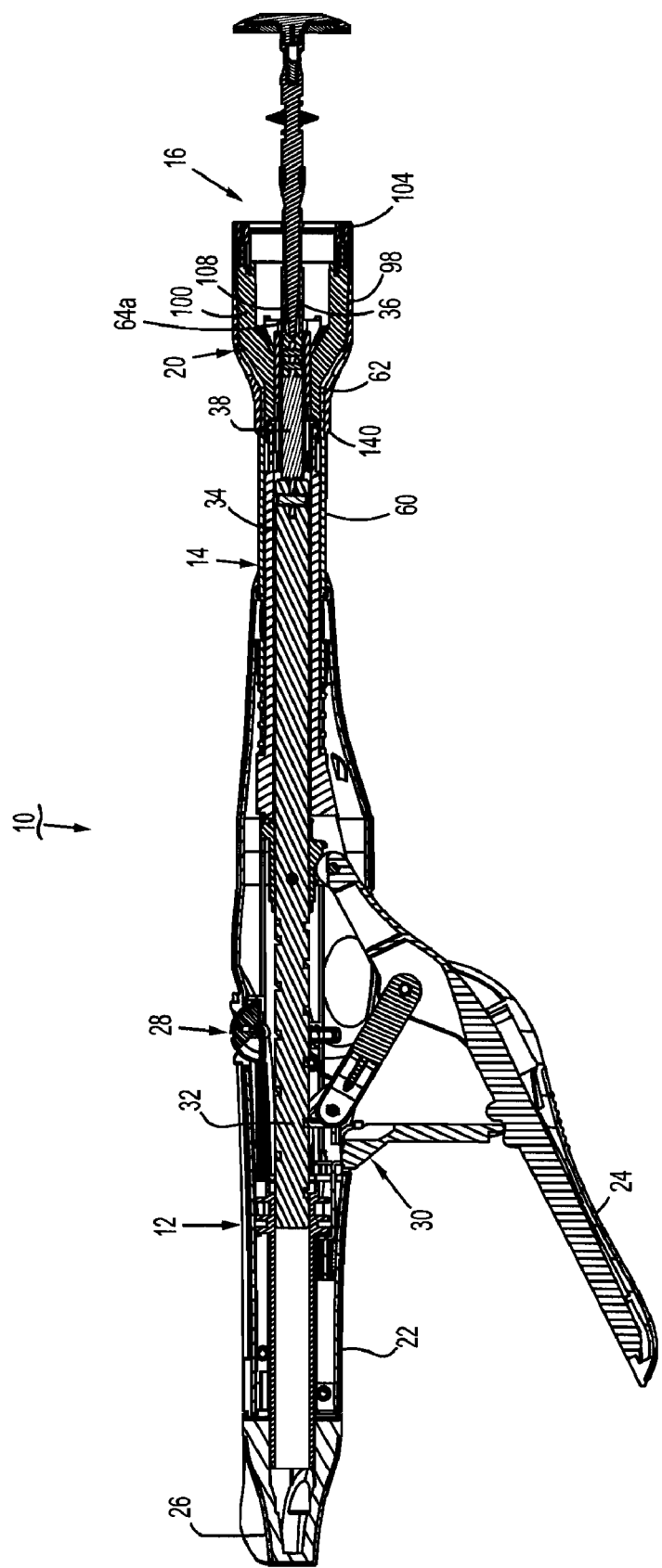
FIG. 1A is a longitudinal cross-sectional view of the surgical stapler of FIG. 1.

FIGS. 1 and 1A illustrate one embodiment of the presently disclosed hemorrhoid stapler 10. Briefly, surgical stapler 10 includes a handle assembly 12, a central body or elongated portion 14 and a distal head portion 16. Head portion 16 includes an anvil assembly 18 and a shell assembly 20. Except where otherwise noted, the components of stapler 10 are generally formed from thermoplastics including polycarbonates, and metals including stainless steel and aluminum. The particular material selected to form a particular component will depend upon the strength requirements of the particular component. For example, the anvil may be formed from a metal such as stainless steel, whereas portions of handle assembly 12 may be formed from thermoplastic such as a polycarbonate. Alternately, other materials having the requisite strength requirements which are suitable for surgical use may be used to form the components of stapler 10.

Handle assembly 12 includes a stationary handle 22, a firing trigger 24, an approximation knob 26, an indicator assembly 28, and a lockout mechanism 30. Approximation knob 26 functions to retract and advance a drive screw 32 to advance or retract anvil assembly 18 in relation to cartridge assembly 20. Firing trigger 24 functions to advance a pusher link 34 to actuate a pusher to eject staples from shell assembly 20. Each of the components of handle assembly 12 identified above are substantially as described in U.S. Pat. No. 7,303,106 ("'106 patent") entitled "Surgical Stapling Device With Visual Indicator" which issued on Dec. 4, 2007. The '106 patent is incorporated herein by reference in its entirety. Accordingly, these components and assemblies will not be described in detail herein.

Figure 1B:
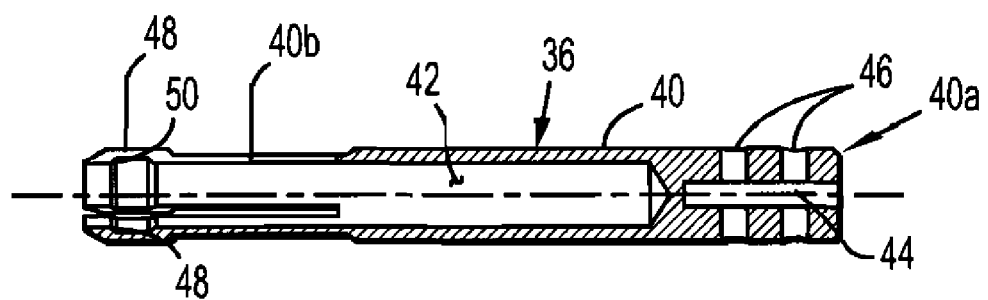
FIG. 1B is a cross-sectional view of the anvil retainer of the stapler of FIG. 1.
Figure 1C:
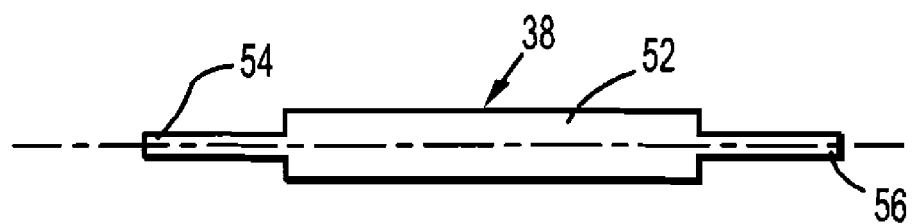
FIG. 1C is a side view of the connector of the stapler of FIG. 1.

Referring to FIGS. 1A-1C, an anvil retainer 36 is secured to a distal end of drive screw 32 by a connector 38. Anvil retainer 36 includes a body 40 defining an elongated bore 42. A proximal end 40a of body 40 includes a longitudinal slot 44 and a pair of transverse throughbores 46. A distal end 40b of body 40 includes three segmented flexible arms 48. Each of the arms 48 has an inner retention surface 50 which will be described in further detail below.

Connector 38 includes a central body 52 having a proximal extension 54 and a distal extension 56. Proximal extension 54 is dimensioned to be received within a slot (not shown) formed in the distal end of drive screw 32. Extension 54 and the distal end of drive screw 32 each define a transverse throughbore for receiving a pin, rivet, screw or the like 60 for fixedly securing connector 38 to drive screw 32. Distal extension 56 is dimensioned to be received within slot 44 of body 40 of anvil retainer 36. Extension 56 includes a pair of spaced throughbores which align with throughbores 46 of anvil retainer 36 and are dimensioned to receive pins, screws, rivets or the like 62 to fixedly secure anvil retainer 36 to connector 38. Although pins, screws, rivets or the like are specifically disclosed for securing connector 38 to drive screw 32 and anvil retainer 36, other known fastening techniques are envisioned, e.g., welding, crimping, and interlocking structure. In an alternate embodiment, the connector and anvil retainer can be replaced with a single part, e.g. an elongated anvil retainer, having an extended length to function similarly to the extended length resulting from the provision of connector 38.

Figure 2:
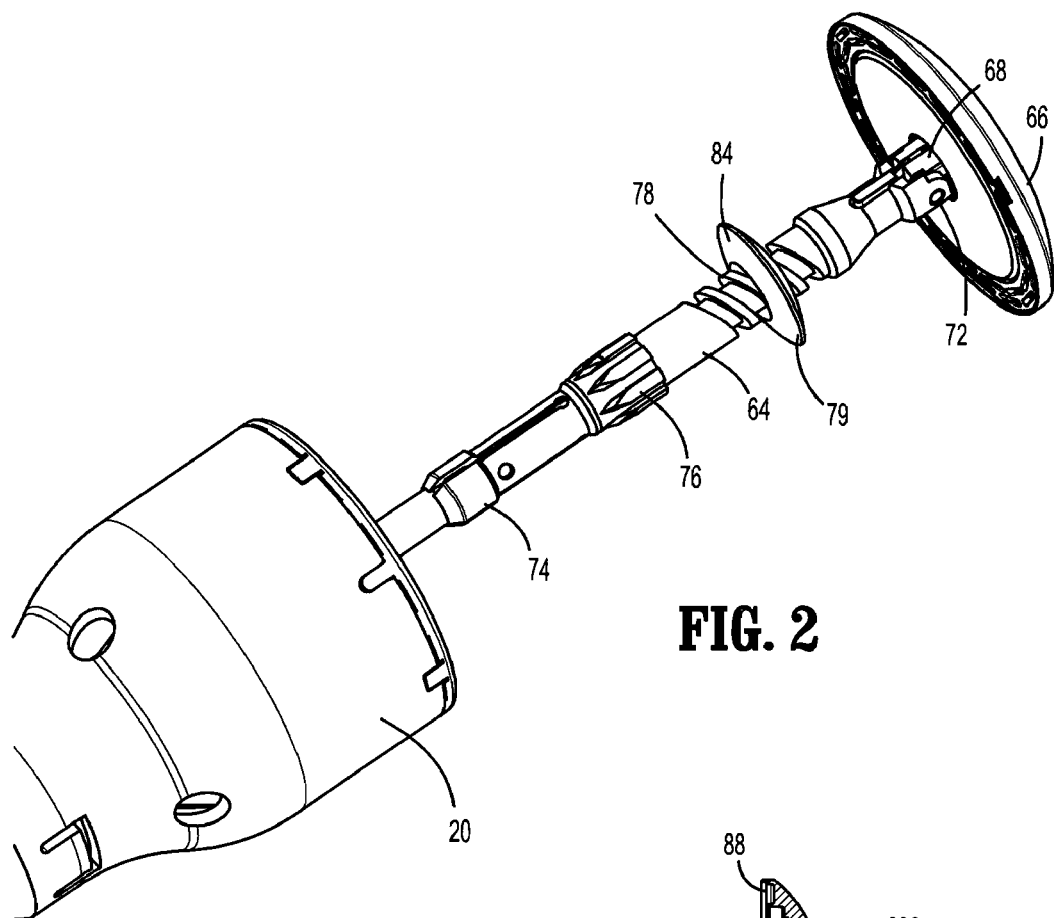
FIG. 2 is a close up perspective view of the anvil assembly and shell assembly of FIG. 1.

Referring to FIGS. 2 and 5, anvil assembly 18 includes an anvil shaft or center rod 64 and an anvil head 66. Anvil shaft 64 includes a tapered proximal blunt end 64a (FIG. 1A) and an opposite distal end for mounting to anvil post 68 of anvil head 66. A pin 72 (or alternatively a screw, rivet or the like) mounts the anvil post 68 to anvil shaft 64. It should be appreciated, that anvil post 68 can be pivotally mounted to anvil shaft 64 so that the anvil can move between an operative non-tilted position to a tilted position. This is described in detail in U.S. Pat. No. 7,303,106, the entire contents of which is incorporated herein by reference. Alternatively the anvil can be fixedly (non-pivotably) mounted to the anvil shaft 64.

Anvil shaft 64 includes a stepped surface or ring 74 which is configured to engage retention surfaces 50 (FIG. 1B) of flexible arms 48 to releasably secure anvil shaft 64 to anvil retainer 36. An orientation groove or grooves is provided in anvil shaft 64 beneath spines 76 to effect proper alignment of splines 76 about shaft 64 to facilitate proper alignment of anvil assembly 18 and shell assembly 20 when anvil assembly 18 is retracted towards shell assembly 20.

Anvil shaft 64 also includes over-molded splines 76. Splines 76 function as known in the art to properly align anvil assembly 18 with shell assembly 20 (FIG. 1). Alternatively, the anvil shaft can have machined splines.

Anvil shaft 64 has a helical cam slot or groove 78 formed therein. An adjustable movable member 79 having an internal thread 81 engages the helical slot 78 on the anvil shaft 64. The movable member 79 is rotated to slide in an adjustable nut fashion either distally or proximally along slot 78 and therefore along anvil shaft 64 to adjust the positioning of the purse string and/or the tension on the purse string as described below.

Figure 3A:
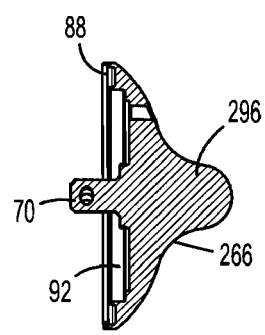
FIG. 3 is a perspective view of the disc of FIG. 1.
Figure 3:
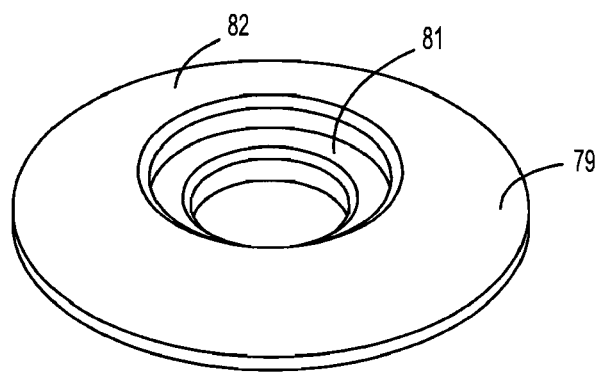

In the embodiment of FIGS. 2 and 3, the movable (rotatable) member is in the form of a unitary disc 79. In the alternate embodiment of FIG. 4, disc 179 is composed of two components 179a, 179b. The components 179a, 179b are shown attached by a pin 182/slot 184 arrangement, although other structures for attaching the two components are also contemplated. This two component version 179 eases assembly as each disc half is placed over the anvil shaft 64 and then fitted together. It also enables the disc to be removed by the user if not desired or be provided as an optional accessory to be placed on the anvil shaft if the surgeon desires such selective adjustment of the purse string suture.

The disc is configured to provide a locator for a purse-string suture, creating a region or stop to retain the suture. The disc 79, 179 enables the user to decide the amount of tissue desired for purse stringing, e.g. moving the disc to a more proximal position (i.e. further from the anvil head) would enable additional tissue to be taken and presented for stapling. Thus, the disc can be moved to a selected position prior to securing the purse string around the anvil shaft 64.

The disc 79, 179 can also be used as a tissue tensioner. In this manner, after the purse string suture is placed about the anvil shaft 64, the disc can be rotated along the helical slot (proximally) to apply additional tension to the suture to present additional tissue in the shell assembly for subsequent stapling.

The disc 79 has a distal surface 82 closer to the anvil head and a proximal surface 84 closer to the shell assembly. Both the proximal and distal surfaces 82, 84 are preferably angled, with the distal surface angled such that the surface angles in a proximal direction and the proximal surface angled so the surface angles in a distal direction. This is best shown in FIG. 5.

As discussed above, anvil retainer 36 (FIG. 1B) defines an elongated bore 42 which is dimensioned to receive anvil shaft 64 such that stepped surface 74 of shaft 64 engages retention surface 50 to releasably secure anvil assembly 18 to anvil retainer 36. In one embodiment, anvil shaft 64 is of a length to protrude from the anus when properly positioned during a surgical procedure to treat colon prolapse. By protruding from the anus, the interface between the anvil shaft 64 and anvil retainer 36 is exposed and visible for attachment. For example, in one embodiment, shaft 64 extends outwardly from a face 86 (FIG. 2) of anvil head 66 a distance greater than about three inches, and for example extends outwardly from face 86 of anvil head 66 a distance of about 3.55 inches. In another embodiment, the shaft extends outwardly a distance of greater than about five inches, and for example extends about 5.234 inches.

Anvil head 66 is shown with a low distal profile, however, other shapes are contemplated such as the bulbous, smoothly contoured anvil 266 illustrated in FIG. 3A. Bulbous portion 296 facilitates insertion of head 266 through a purse string suture. The anvil head 266 can be attached to the anvil shafts disclosed herein.

Figure 1D:
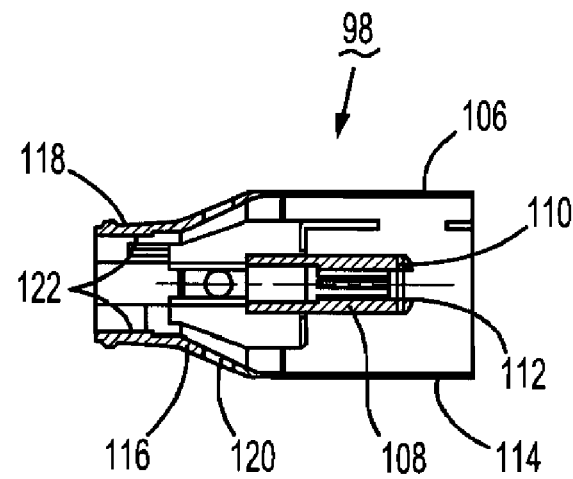
FIGS. 1D and 1E are cross-sectional views of portions of the shell assembly of FIG. 1.
Figure 1E:
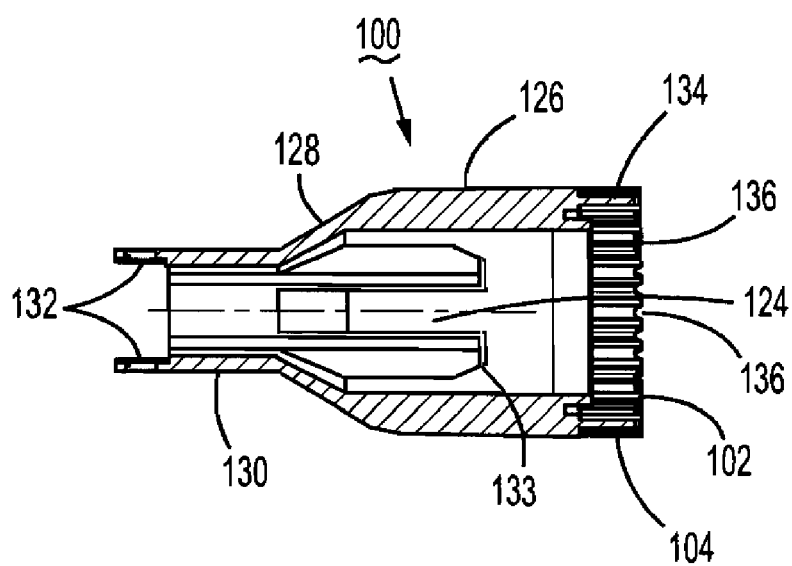

Referring to FIGS. 1A, 1D and 1E, shell assembly 20 is secured to the distal end of central body portion 14 in a manner substantially similar to that described in the '106 patent incorporated herein by reference. Shell assembly 20 includes a shell or housing 98, a pusher back 100, a cylindrical knife 102, and a staple guide 104. Staple guide 104 houses one or more rows of staples (not shown).

Shell 98 includes an outer housing portion 106 and an inner guide portion 108 having grooves 110 for mating with splines 76 on anvil shaft 64. Outer housing portion 106 defines a throughbore 112 having a distal cylindrical section 114, a central conical section 116 and a proximal smaller diameter cylindrical section 118. A plurality of openings 120 are formed in conical section 116. Openings 116 are dimensioned to permit fluid and tissue passage during operation of stapler 10. A pair of diametrically opposed flexible engagement members 122 are formed on proximal cylindrical section 118 of shell 98. Engagement members 122 are positioned to be received in openings formed on a distal end of body portion 14 to secure shell 98 to body portion 14. Vent holes 29 (FIG. 1) are provided in shell assembly 20.

Pusher back 100 includes a central throughbore 124 which is slidably positioned about inner guide portion 108 of shell 98. Pusher back 100 includes a distal cylindrical section 126 which is slidably positioned within distal cylindrical section 114 of shell 98, a central conical section 128 and a proximal smaller diameter cylindrical section 130. The proximal end of pusher back 100 includes members 132 which are configured to lockingly engage with a pusher link of stapler 10 as described in the '106 patent incorporated by reference herein. Pusher back 100 also defines a receptacle 133 for receiving excised tissue. Receptacle 133 is configured to have a depth of between about 0.75 inches and about 2.00 inches. In one embodiment, receptacle 133 has a depth of about 1.33 inches.

The distal end of pusher back 100 includes a pusher 134 (FIG. 1E). Pusher 134 includes a multiplicity of distally extending fingers 136 dimensioned to be slidably received within slots (not shown) formed in staple guide 104 to eject staples (not shown) therefrom. Cylindrical knife 102 is retained within the central throughbore of pusher back 100 to fixedly secure knife 102 in relation to pusher 134. Knife 102 may be retained within pusher back 100 using adhesives, crimping, pins, friction, etc. The distal end of knife 102 includes a circular cutting edge.

The rigid bushing 140 is supported in the proximal end of inner guide portion 108 of shell 98. Bushing 140 defines a throughbore dimensioned to slidably receive anvil retainer 36 and anvil shaft 64 of anvil assembly 18. Bushing 140 provides lateral support for flexible arms 48 of anvil retainer 36 when the anvil assembly 18 has been approximated to prevent disengagement of anvil assembly 18 from anvil retainer 36. In the unapproximated position, flexible arms 48 are positioned externally of bushing 140 to permit flexing of the arms for removal of anvil assembly 18 from retainer 36.

Figure 6:
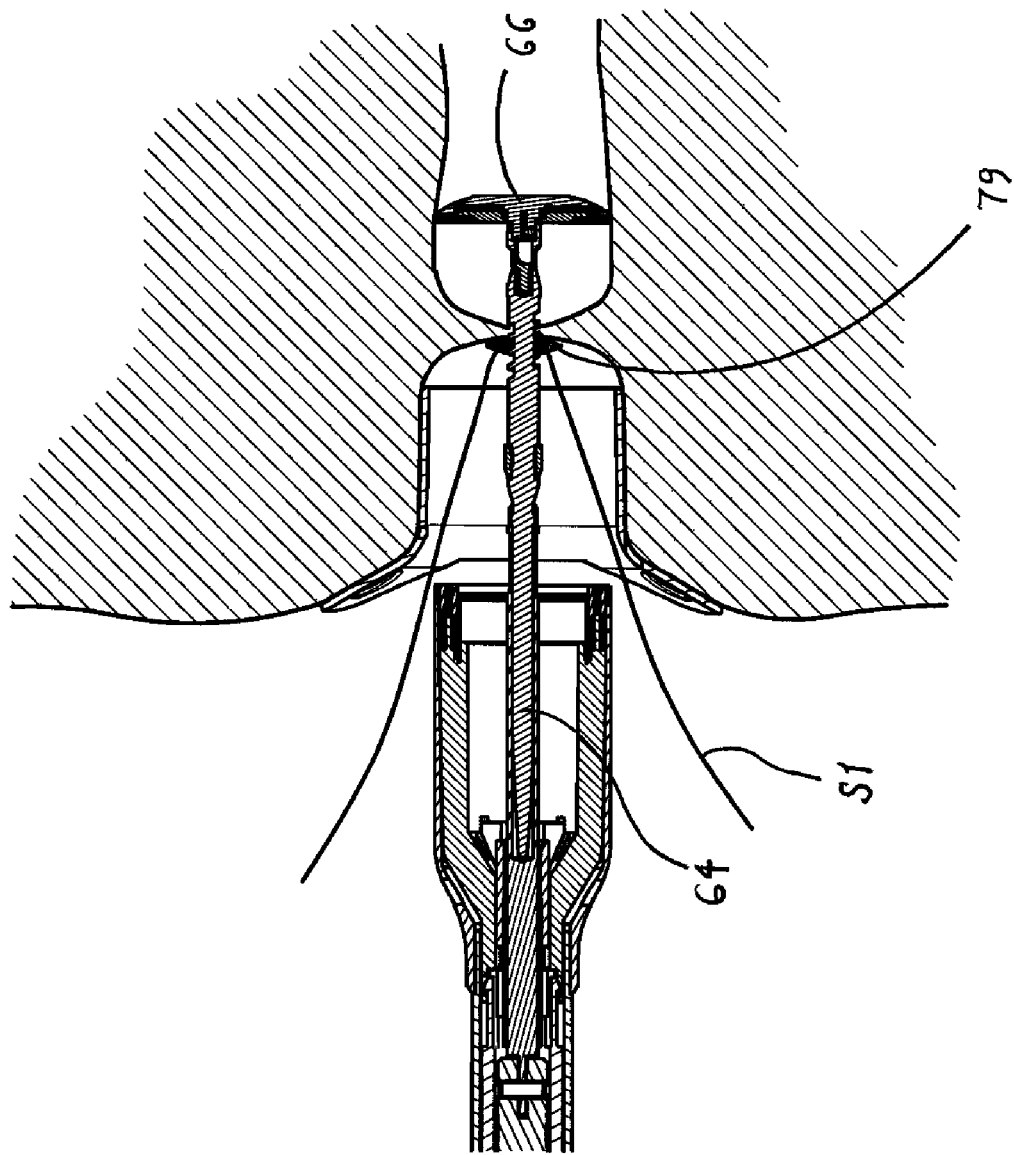
FIG. 6 is a side view illustrating placement of the purse string suture in an anvil assembly of the present disclosure.

As discussed above, stapler 10 is particularly suitable for use in surgical procedures for treating colon prolapse. During such procedure, an access port can be inserted into the anus to facilitate access to the prolapsed colon. Next, a purse string suture is placed into, above or in the vicinity of the colon prolapse. Disc member 79 (or 179) is rotated for movement along the anvil shaft 64 to a selected position, depending on the amount of tissue desired to be drawn in the shell assembly and presented for stapling, and the anvil assembly 18 is inserted through the access portion into the anus and rectum. Thereafter, the purse string suture (FIG. 6) is placed about the anvil shaft 64 abutting the disc 79, 179 which retains the suture position. A greater amount of tissue will be drawn into shell assembly 20 by retaining the purse string suture against a more proximal position of the disc. The suture ends are tightened and pulled toward the user, therefore pulling the tissue proximally. The surgeon can then visualize the tissue to be stapled, i.e. the tissue donut to be removed. The stapling instrument, e.g. instrument 10 of FIG. 1, is inserted through the port and attached to the anvil assembly, with the elongated anvil shaft and elongated instrument shaft providing increased visibility. At any point, if desired, the disc 79, 179 can be rotated to a more proximal position to apply additional tension on the suture. Anvil assembly 18 and shell assembly 20 are then approximated via knob 26 to draw the prolapsed colon into shell assembly 20.

When surgical stapler 10 is fully approximated, firing trigger 24 can be actuated or fired in a manner described in the '106 patent to staple, sever and allow removal of a portion of the prolapsed colon. Thereafter, the stapler is at least partially unapproximated and removed from the anus with the excised tissue contained within receptacle 133 of pusher back 100 within shell assembly 20. In the embodiments where a tilting anvil is used, after the firing step and sufficient movement of the anvil away from the shell assembly 20, the anvil will tilt (not shown) to its inoperative position to facilitate removal.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended hereto.

What is claimed is:

1. An anvil assembly comprising an anvil shaft and an anvil head, the anvil head having anvil depressions for forming surgical staples, the anvil head mounted to the anvil shaft, the anvil shaft having a longitudinal axis and a helical slot formed therein, and a rotatable disc, composed of two separate components, the two separate components being attachable about the anvil shaft such that the disc is movable along the slot to a selected position to selectively adjust the positioning of a purse string suture.

2. The anvil assembly of claim 1, wherein the two components of the disc are attached by a pin and slot arrangement.

3. The anvil assembly of claim 1, further comprising a mounting structure on the anvil shaft for releasably mounting the anvil shaft to a stapling instrument.

4. The anvil assembly of claim 1, wherein the rotatable disc has a convex surface on a proximal side.

5. The anvil assembly of claim 1, wherein the rotatable disc has a convex surface on a distal side.

6. The anvil assembly of claim 1, wherein a distal surface and a proximal surface of the disc are angled.

7. A surgical stapler comprising;
   a handle assembly;
   an elongated body portion extending distally from the handle assembly; and
   a head portion disposed adjacent a distal end of the elongated body portion and including an anvil assembly and a shell assembly, the anvil assembly being movable in relation to the shell assembly between spaced and approximated positions, the anvil assembly having an anvil head and an anvil shaft having a helical slot formed therein, a rotatable disc composed of two components attachable to each other about the anvil shaft such that the disc is movable along the slot to a selected position to adjust the amount of tissue drawn into the shell assembly by a purse string suture.

8. The surgical stapler of claim 7, wherein the rotatable disc has a convex surface on a proximal side.

9. The surgical stapler of claim 7, wherein the rotatable disc has a convex surface on a distal side.

10. The surgical stapler of claim 9, wherein the anvil shaft is removably mounted to an anvil retainer of the stapler.

11. The surgical stapler of claim 7, wherein a distal surface and a proximal surface of the disc are angled.

* * * * *